(12) United States Patent
Kalyanpur et al.

(10) Patent No.: US 10,803,149 B2
(45) Date of Patent: Oct. 13, 2020

(54) SYSTEM AND METHOD FOR CONTROLLED MEDICAL THERAPY

(71) Applicant: Validose Inc., Brooklyn, NY (US)

(72) Inventors: Arjun Kalyanpur, New York, NY (US); Kyle Lapidus, Setauket, NY (US); Nicholas Safian, Brooklyn, NY (US); Marcel Botha, Brooklyn, NY (US)

(73) Assignee: Validose Inc., Brooklyn, NY (US)

( * ) Notice: Subject to any disclaimer, the term of this patent is extended or adjusted under 35 U.S.C. 154(b) by 324 days.

(21) Appl. No.: 15/686,713

(22) Filed: Aug. 25, 2017

(65) Prior Publication Data

US 2018/0060527 A1    Mar. 1, 2018

Related U.S. Application Data

(60) Provisional application No. 62/379,523, filed on Aug. 25, 2016.

(51) Int. Cl.
*G06F 19/00* (2018.01)
*G16H 20/13* (2018.01)
(Continued)

(52) U.S. Cl.
CPC ....... *G06F 19/3462* (2013.01); *A61M 11/007* (2014.02); *G06F 21/32* (2013.01);
(Continued)

(58) Field of Classification Search
CPC .......... A61M 11/007; A61M 2205/276; A61M 11/08; A61M 15/0081; E05B 17/22;
(Continued)

(56) References Cited

U.S. PATENT DOCUMENTS 6,032,155 A    2/2000  de la Huerga
6,196,219 B1   3/2001  Hess et al.
(Continued)

FOREIGN PATENT DOCUMENTS

DE    102013202933 B3    11/2013
DE    202016003139 U1     6/2016
(Continued)

OTHER PUBLICATIONS

Communication from the European Patent Office, PCT/US2017/048624, pp. 1-8, dated Mar. 18, 2020.
(Continued)

*Primary Examiner* — Samchuan C Yao
*Assistant Examiner* — Nathan M Le
(74) *Attorney, Agent, or Firm* — Bond Schoeneck & King, PLLC; George McGuire

(57) ABSTRACT

The present invention relates to a system and method for dispensing medication through a time controlled device linked to a web platform. The system includes a dispensing device in wireless communication with a computing device. A web platform on the computing device can be used to program the dispensing device with parameters such as the dosage number, minimum time period between dosages, and the like. Based on the programmed parameters, a solenoid in the dispensing device will lock or unlock based on dosages administered and the time between dosages.

14 Claims, 13 Drawing Sheets

(51) Int. Cl.
*G16H 40/63* (2018.01)
*A61M 11/00* (2006.01)
*G06F 21/32* (2013.01)
*G06Q 10/10* (2012.01)

(52) U.S. Cl.
CPC ............. *G16H 20/13* (2018.01); *G16H 40/63* (2018.01); *A61M 2205/276* (2013.01); *A61M 2205/50* (2013.01); *A61M 2205/502* (2013.01); *A61M 2205/505* (2013.01); *A61M 2205/582* (2013.01); *A61M 2205/584* (2013.01); *A61M 2205/609* (2013.01); *A61M 2205/8206* (2013.01); *G06Q 10/109* (2013.01)

(58) Field of Classification Search
CPC .... E05B 17/044; E05B 17/045; E05B 17/046; G16H 20/13; G16H 20/60; G16H 20/70; G16H 20/90
See application file for complete search history.

(56) References Cited

U.S. PATENT DOCUMENTS

| | | | |
|---|---|---|---|
| 6,435,175 | B1 | 8/2002 | Stenzler |
| 6,886,556 | B2 | 5/2005 | Fuchs |
| 7,100,601 | B2 | 9/2006 | Bruna |
| 7,335,186 | B2 | 2/2008 | O'Neil |
| 7,806,852 | B1 | 10/2010 | Jurson |
| 7,996,106 | B2 | 8/2011 | Ervin |
| 8,252,329 | B2 | 8/2012 | Tzannis et al. |
| 8,785,500 | B2 | 7/2014 | Charney et al. |
| 9,033,939 | B2 | 5/2015 | Eberhart et al. |
| 9,061,879 | B2 | 6/2015 | Patthey |
| 9,329,553 | B2 | 5/2016 | Taniguchi |
| 9,349,233 | B2 | 5/2016 | Muecke et al. |
| 9,352,108 | B1 * | 5/2016 | Reed .................. A61M 15/0091 |
| 9,642,996 | B2 | 5/2017 | Palmer et al. |
| 9,665,691 | B2 | 5/2017 | Ervin |
| 9,984,213 | B2 | 5/2018 | Howieson et al. |
| 2002/0000225 | A1* | 1/2002 | Schuler ................. A61M 15/00 128/200.14 |
| 2004/0231667 | A1* | 11/2004 | Horton .............. A61M 15/0065 128/202.13 |
| 2005/0228341 | A1* | 10/2005 | Edgerley ........... A61M 15/0043 604/59 |
| 2006/0021614 | A1 | 2/2006 | Wermeling et al. |
| 2007/0186923 | A1* | 8/2007 | Poutiatine ........... G06F 19/3462 128/200.14 |
| 2008/0017658 | A1 | 1/2008 | Wright |
| 2008/0041368 | A1* | 2/2008 | Jones ................ A61M 15/0083 128/200.23 |
| 2008/0140250 | A1 | 6/2008 | Dave |
| 2009/0120962 | A1* | 5/2009 | Malorni .............. A61M 15/009 222/153.11 |
| 2009/0139516 | A1* | 6/2009 | Augustyn ............. G06M 1/045 128/200.23 |
| 2010/0084433 | A1* | 4/2010 | Cater ................ A61M 15/0065 222/153.13 |
| 2010/0095957 | A1 | 4/2010 | Corbacho |
| 2013/0072755 | A1* | 3/2013 | Papania ............ A61M 15/0098 600/109 |
| 2013/0239957 | A1* | 9/2013 | Pinfold ................. A61M 11/04 128/200.23 |
| 2014/0081216 | A1* | 3/2014 | Eberhart ................ A61M 11/00 604/246 |
| 2014/0322682 | A1* | 10/2014 | Baym ..................... G09B 7/02 434/219 |
| 2015/0126927 | A1 | 5/2015 | Flickinger |
| 2015/0283337 | A1 | 10/2015 | Adams et al. |
| 2015/0306617 | A1 | 10/2015 | Olegnowicz |
| 2016/0132660 | A1 | 5/2016 | Barajas et al. |
| 2016/0314274 | A1 | 10/2016 | Zieger |
| 2017/0083687 | A1 | 3/2017 | Josyula et al. |

FOREIGN PATENT DOCUMENTS

| | | |
|---|---|---|
| EP | 1328309 | 7/2003 |
| EP | 1721596 | 11/2006 |
| EP | 1749548 | 6/2007 |
| WO | 20170139761 | 8/2017 |

OTHER PUBLICATIONS

International Search Report Form PCT/ISA/210, International Application No. PCT/US2017/048624, pp. 1-10, International Filing Date Aug. 25, 2017, dated Dec. 12, 2017.

\* cited by examiner

SYSTEM AND METHOD FOR CONTROLLED MEDICAL THERAPY

CROSS-REFERENCE TO RELATED APPLICATIONS

The present application claims priority to and the benefit of U.S. Provisional Patent Application No. 62/379,523, filed on Aug. 25, 2016, the entire contents of which are hereby incorporated by reference.

BACKGROUND OF THE INVENTION

1. Field of the Invention

The present invention relates to a system and method for controlling the dispensing of medication, and, more specifically, to a system and method for dispensing medication through a time controlled device linked to a web platform.

2. Description of the Related Art

Conventional personal medication dispensing devices, such as intranasal spray devices, are often effectively used to deliver atomized medications. Traditional intranasal spray devices consist of a pump with an elongated nozzle which atomizes liquid as the liquid is propelled through the nozzle and out the delivery orifice. The resulting mist is inhaled and efficiently absorbed by the tissue, thereby providing an effective treatment.

Intranasal spray devices have been utilized to provide medication for conditions ranging from allergies, pain relief and depression. For conditions such as pain relief and depression, the risk of abuse associated with the medications provided within the device is high due to the addictive nature of medication treating those conditions. Ketamine, for example, has shown great effectiveness in treating serious conditions such as bipolar depression. However, given the addictive nature of medications such as ketamine, healthcare providers are hesitant to administer or otherwise prescribe them for home use. Healthcare providers are often concerned with patients abusing or misusing the medication, a person other than the patient abusing the medication, and theft and/or sale of the medication.

Abuse and misuse is not only attributed to the addictive nature of the medications but also the efficacy of the medication at delivering relief for the patient's condition. Patients may be driven to use more than their prescribed dosage due to the relief the medication provides. Consequently, patients in need of such medications may only receive a small dosage or supply per visit to a healthcare provider. As a result, some patients must visit their healthcare provider frequently, such as multiple times per week. Numerous required visits to a healthcare provider are not only inconvenient, but can also act as a barrier to access to medication for those who cannot afford burdensome transportation or take extended time away from their place of employment.

BRIEF SUMMARY OF THE INVENTION

The present invention is a system and method for dispensing medication through a time controlled device linked to a web platform. The system includes a dispensing device and a computing device. The dispensing device comprises a cylindrical housing having a first closed end and a second closed end. The first closed end comprises a first surface with a nozzle extending perpendicular therefrom. The second closed end comprises a baseplate secured to the housing with fasteners. The housing further comprises a recess with a display screen therein.

The housing may additionally comprise a cylindrical liquid container therein configured to store liquid medicinal compositions. The liquid container comprises a pump assembly configured to propel the liquid medicinal composition through a channel in the nozzle. The housing also comprises a locking mechanism, such as a solenoid which operates perpendicular to the motion of the pump assembly. When the solenoid is extended to a locked position, it blocks the path of the nozzle. Therefore, when the solenoid is extended, the nozzle cannot be fully depressed and the liquid medicinal composition cannot be expelled from the dispensing device.

A printed circuit board located within the housing operates the locking mechanism. The printed circuit board is also operably connected to a tactile switch on the pump assembly and a real-time clock. When the pump assembly is actuated, the tactile switch and the real-time clock transmit data signals to the printed circuit board. Using this data, the printed circuit board will lock and unlock the locking mechanism.

The method comprises the steps of programming the printed circuit board with instructions, such as a dosage number and a minimum time period between dosages, programming a user identity based on biometrics or other authentication parameters, receiving a signal from a biometric sensor, moving the locking mechanism to the unlocked position, dispensing a liquid medicinal composition, and moving the locking mechanism to the locked position.

BRIEF DESCRIPTION OF THE SEVERAL VIEWS OF THE DRAWING(S)

The present invention will be more fully understood and appreciated by reading the following Detailed Description in conjunction with the accompanying drawings, in which.

DETAILED DESCRIPTION OF THE INVENTION

Figure 1:
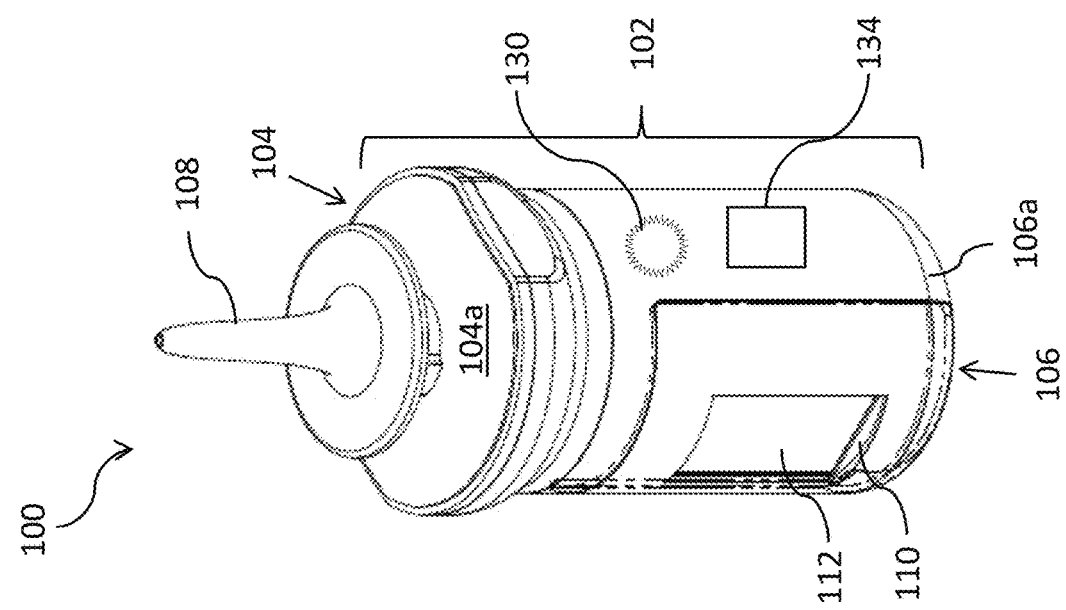
FIG. 1 is a perspective view of an embodiment of the system according to the present invention.
Figure 1:
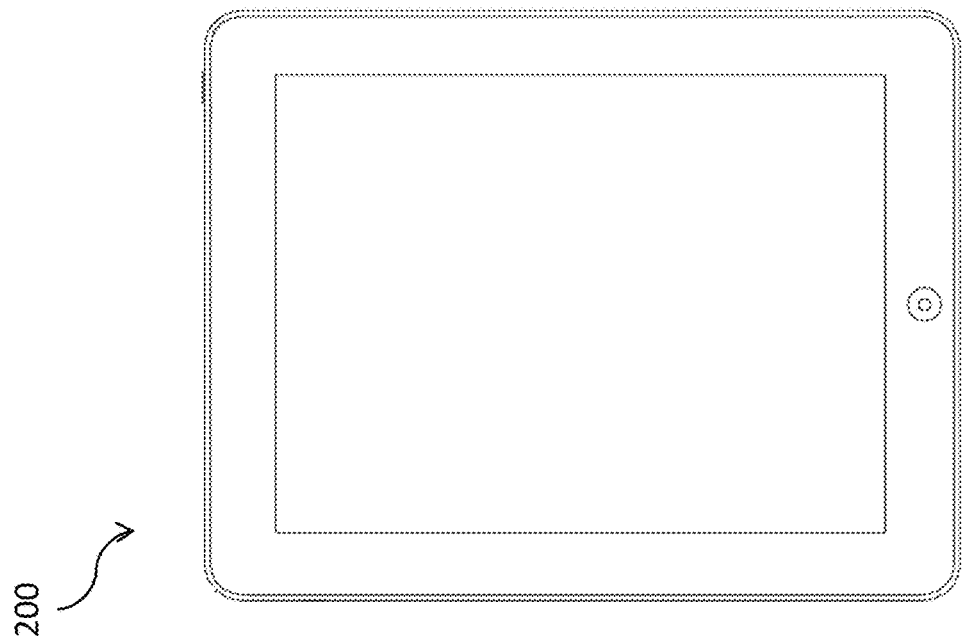

Referring to the Figures, the present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Referring again to the drawings, wherein like reference numerals refer to like parts throughout, there is seen in FIG. 1 a perspective view of an embodiment of the system according to the present invention. FIG. 1 shows an embodiment of the system comprising a dispensing device 100 and a computing device 200. The computing device 200 may be a smartphone, portable tablet, laptop computer, desktop computer, and any other like devices. FIG. 1 also shows the exterior components of an embodiment of the dispensing device 100. The dispensing device 100 comprises a cylindrical housing 102 having a first closed end 104 and a second closed end 106. A nozzle 108 extends perpendicular from a surface 104a of the first closed end 104. The second closed end 106 may further comprise a baseplate 106a secured to the housing 102 with fasteners such as star screws, which will prevent easy tampering with the housing 102. Other fasteners are contemplated such as magnetic fasteners, custom "keyed" screws, or similar locking devices. The housing 102 further comprises a recess 110 with a display screen 112 therein. The display screen may be a panel display, such as a monochrome OLED graphic display, or other LED displays, for example.

Figure 2:
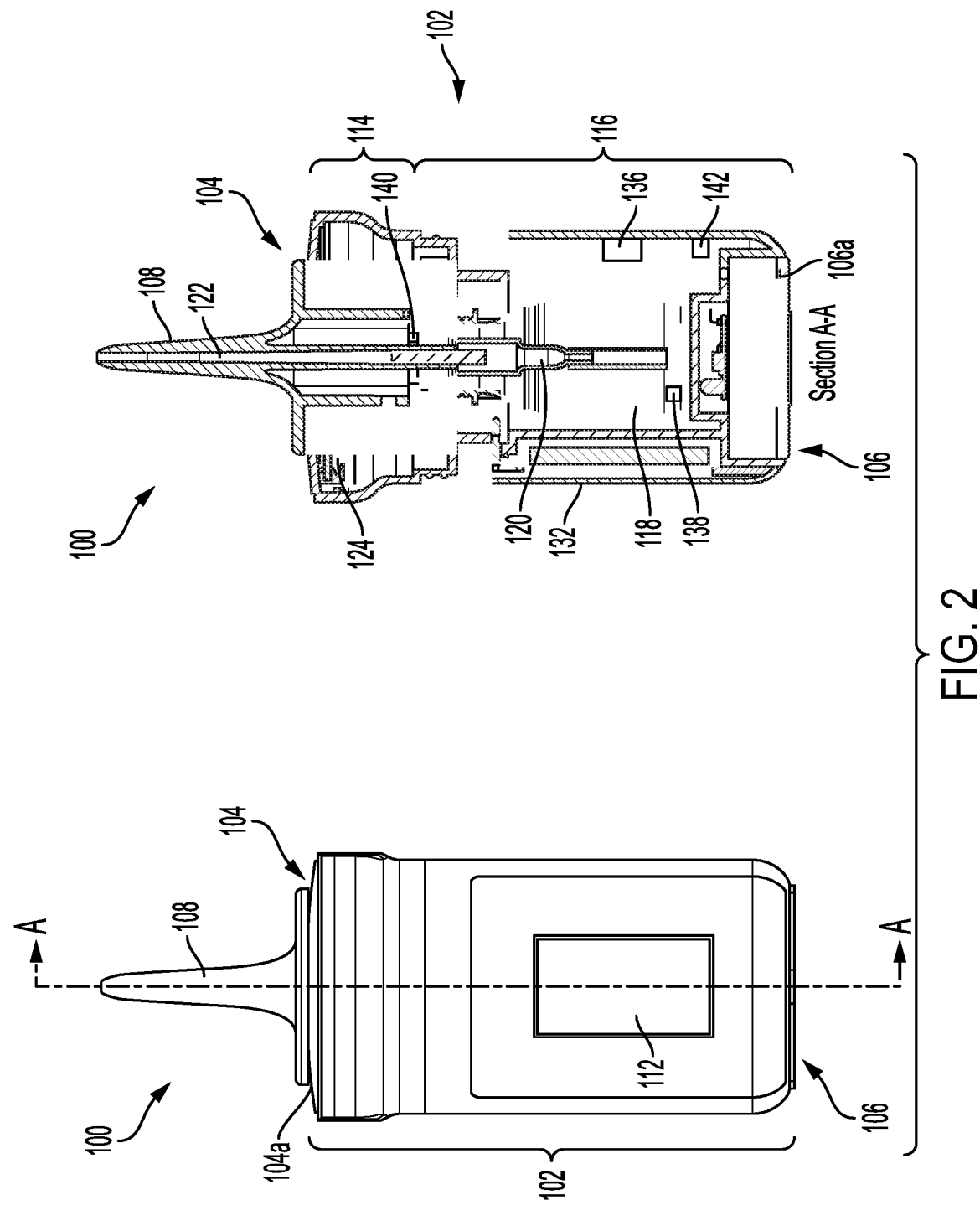
FIG. 2 is a schematic cross-sectional representation of an embodiment of the system in an unlocked position, taken along line A.

Referring to FIG. 2, there is shown a schematic cross-sectional representation of an embodiment of the system in an unlocked position, taken along line A. FIG. 2 shows the interior components of the dispensing device 100 in an unlocked position wherein the nozzle 108 is depressed. The housing 102 of the dispensing device 100 further comprises a first portion 114 and a second portion 116. The first portion 114 of the housing 102 is connected to both the first closed end 104 and the second portion 116.

In the depicted embodiment, the second portion 116 of the housing 102 is connected to the second closed end 106 or the baseplate 106a and provides a base for the dispensing device 100. The second portion 116 houses the liquid container 118, which is configured to store liquid medicinal compositions. In the depicted embodiment, the liquid container 118 is cylindrical such to provide an efficient fit within the similarly cylindrical housing 102. An example of a cylindrical liquid container 118 is a thread size stock vial.

In order to provide access to the medicinal contents of the liquid container 118, the liquid container 118 comprises a pump assembly 120. In the embodiment shown in FIGS. 2A-2B, the pump 120 is centrally located within the liquid container 118. The pump assembly 120 is structured and operates substantially as standard pump assemblies used in conventional intranasal spray devices. As pressure is applied on the nozzle 108 towards the surface 104a of the first closed end 104, the pump assembly 120 propels the liquid medical composition stored within the liquid container 118 through a channel 122 in the nozzle 108, expelling the liquid medical composition from the dispensing device 100. Thus, in an unlocked position, the liquid medical composition can be freely expelled from the dispensing device 100.

Figure 3A:
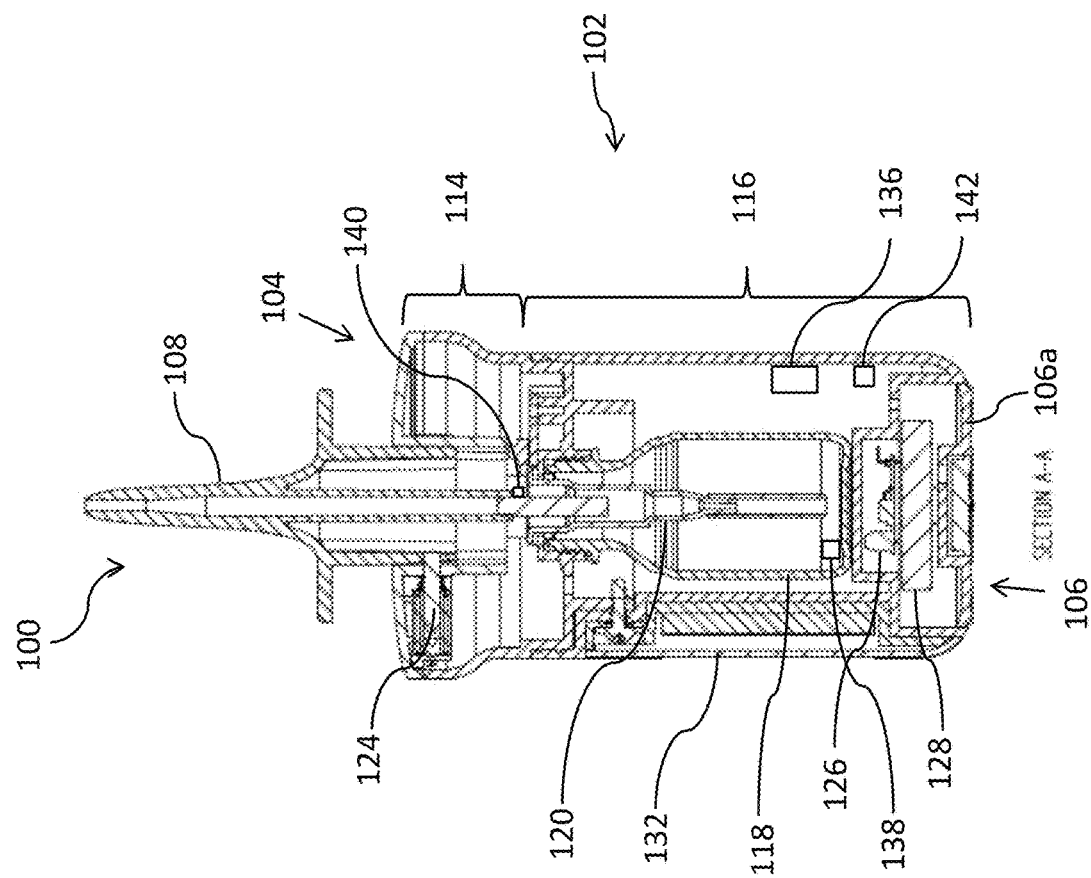
FIG. 3A is a schematic cross-sectional representation of an embodiment of the system in a locked position, taken along line A.
Figure 3A:
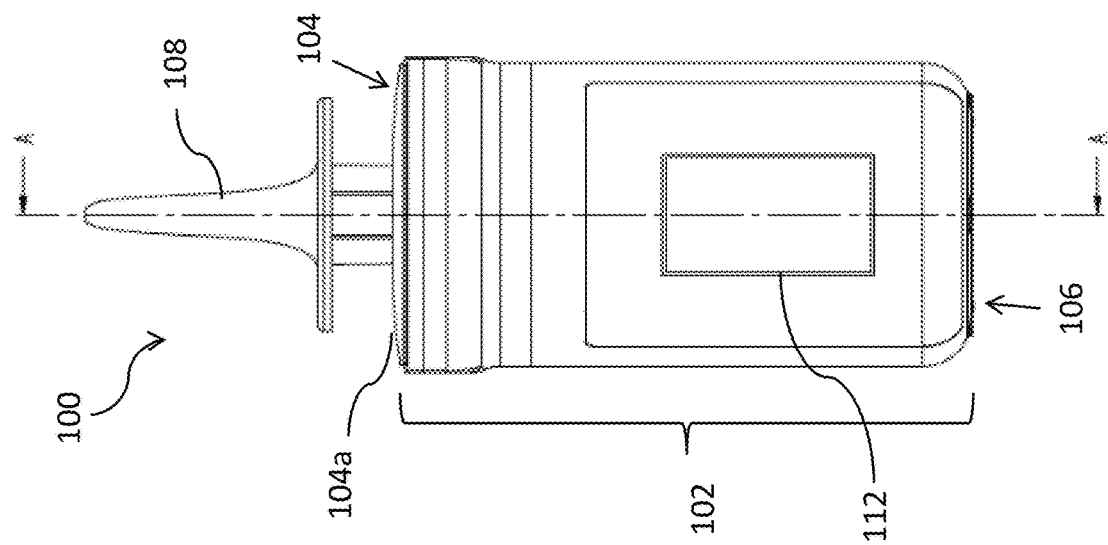
Figure 3B:
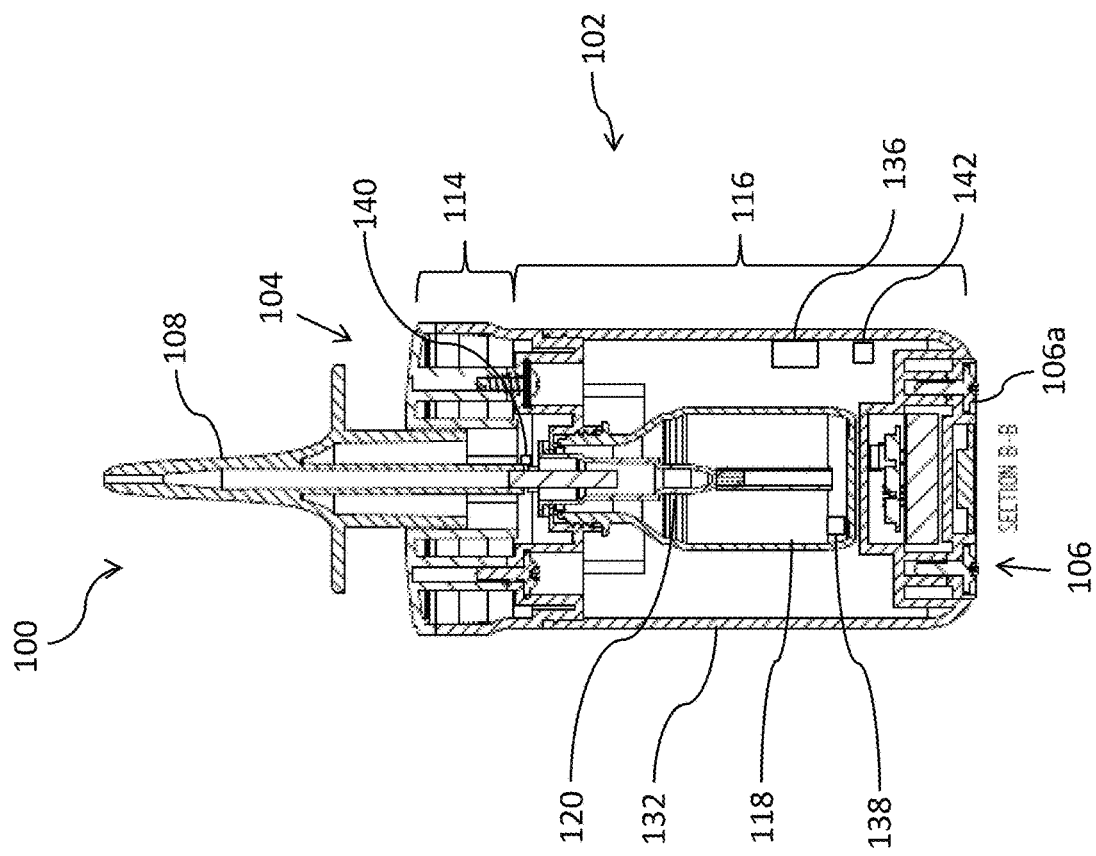
FIG. 3B is a schematic cross-sectional representation of an embodiment of the system in a locked position, taken along line B.
Figure 3B:
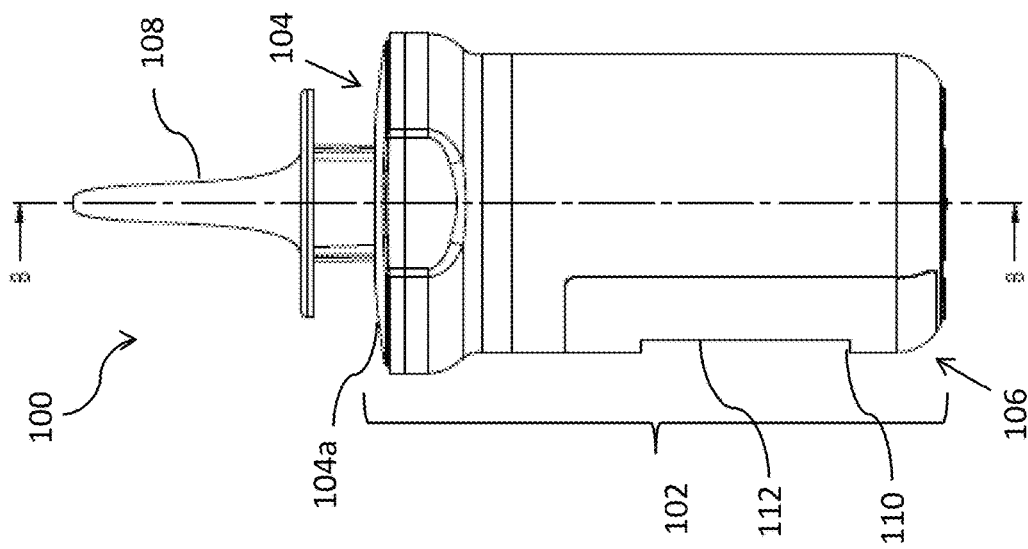

Referring to FIGS. 3A-3B, there are shown schematic cross-sectional representations of an embodiment of the system in a locked position, taken along lines A and B, respectively. In the depicted embodiment, the first portion 114 of the housing 102 further comprises a solenoid 124 locking mechanism therein. The solenoid 124 operates perpendicular to the motion of the pump assembly 120. In one embodiment, when the solenoid 124 is activated, it moves into the path of the nozzle 108 thereby blocking full movement of the nozzle 108 towards the surface 104a of the first closed end 104 and preventing the pump assembly 120 from expelling the liquid medicinal composition from the dispensing device 100. The solenoid 124 is shown in an unlocked position in FIG. 2 and a locked position in FIGS. 3A-3B. In alternative embodiments, the solenoid 124 may comprise attachments such as a U-clip which blocks the path of the nozzle 108 and interrupts the motion of the pump assembly 120.

Referring still to FIGS. 3A-3B, in the depicted embodiment, the solenoid 124 is activated in response to an electrical signal sent from a processor, such as a printed circuit board 126. As shown in FIGS. 3A-B, the printed circuit board 126 is located within the second portion 116 of the housing 102 towards the second closed end 106. The printed circuit board 126 is operably connected to and powered by a battery 128 also located within the second portion 116 at the second closed end 106. The battery 128 can be a rechargeable lithium ion battery or a similar type power source.

Figure 7A:
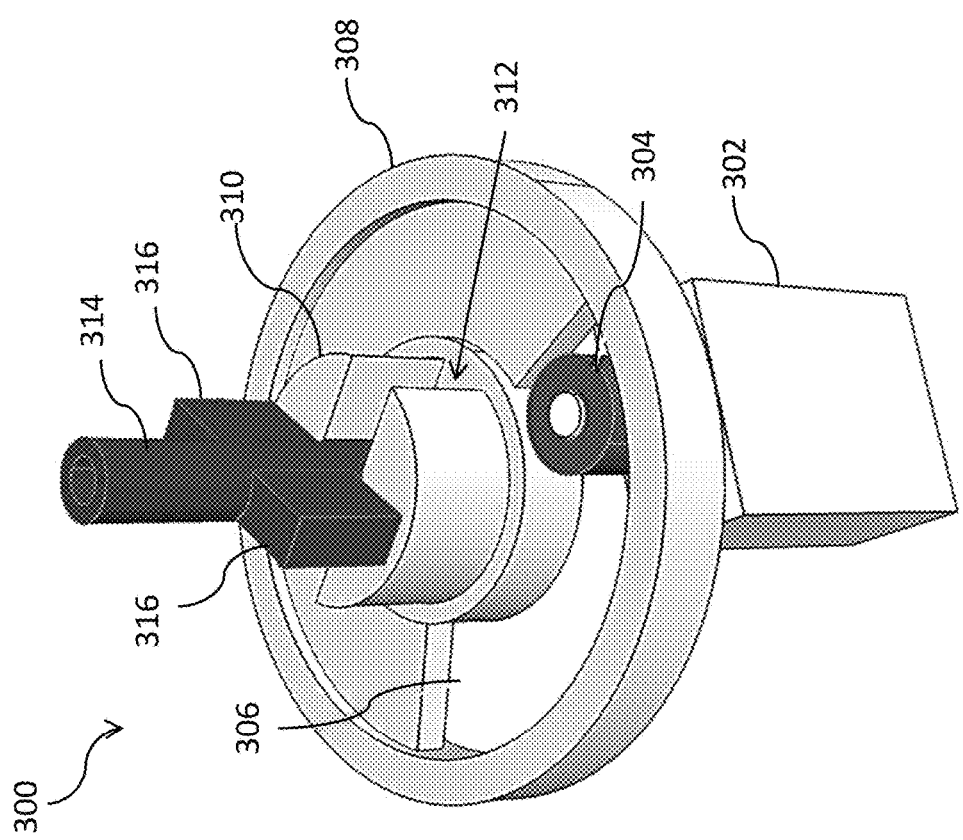
FIG. 7A is a top perspective view of an embodiment of the motor assembly in the locked position.

In an alternative embodiment, the locking mechanism is a motor assembly 300. In FIGS. 7A-8C, there are shown various views of an embodiment of the motor assembly 300 locking mechanism. Referring first to FIG. 7A, a top perspective view of the motor assembly 300 is shown in the locked position. The motor assembly 300 comprises a motor 302 connected to a first gear 304, which is positioned within an opening 306 of an internal gear wheel 308. The internal gear wheel 308 comprises a central lock 310 with a keyway 312 extending therethrough. Similar to the embodiment wherein the locking mechanism is a solenoid 124 (FIGS. 3A-3B), the motor assembly 300 interrupts or otherwise blocks the motion of the pump assembly 120. In the embodiment shown in FIG. 7A, the shaft 314 of a pump assembly 120 extends through the central lock 310 of the internal gear wheel 308. To facilitate locking, there are one or more keys 316 protruding from the shaft 314 of the pump assembly 120. The keys 316 are configured or otherwise fitted to slide into the keyway 312 of the central lock 310. In the embodiment shown in FIG. 7A, the keys 316 rest on the central lock 310 and are blocked from sliding into the keyway 312. Therefore, a nozzle 108 attached to the pump assembly 120 is not compressible when the keys 316 are not in alignment with the keyway 312.

Figure 7B:
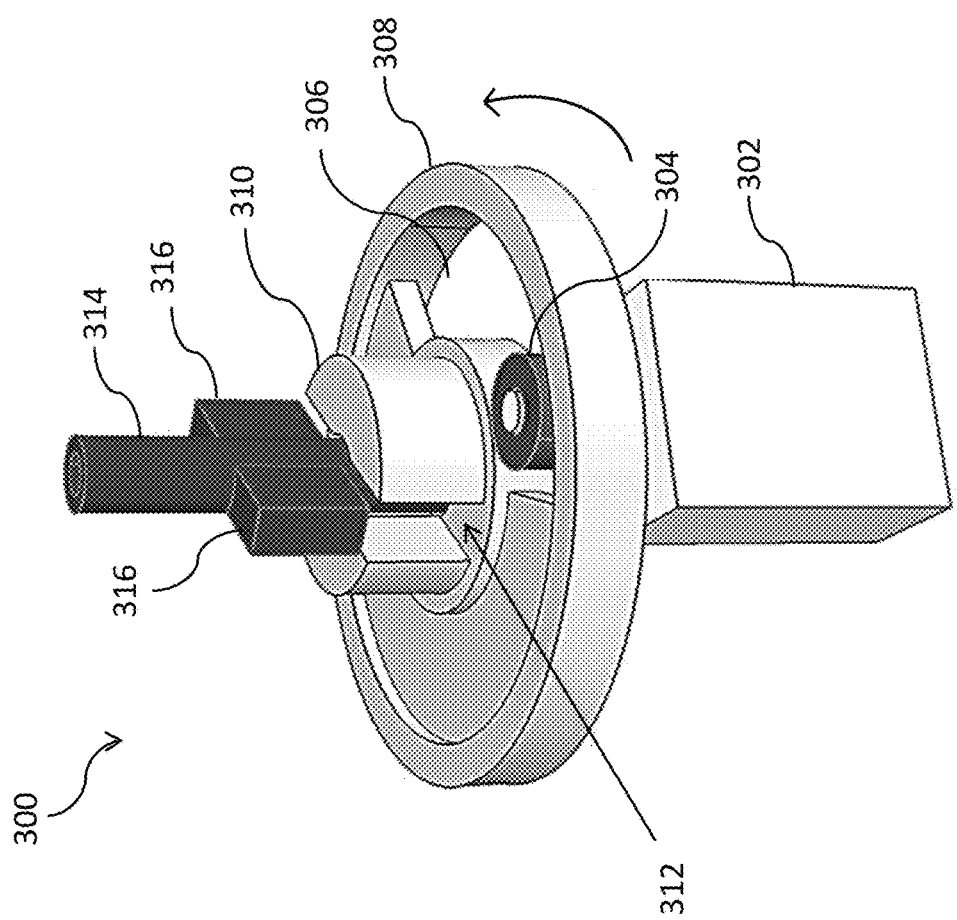
FIG. 7B is a side perspective view of an embodiment of the motor assembly in the unlocked position.
Figure 7C:
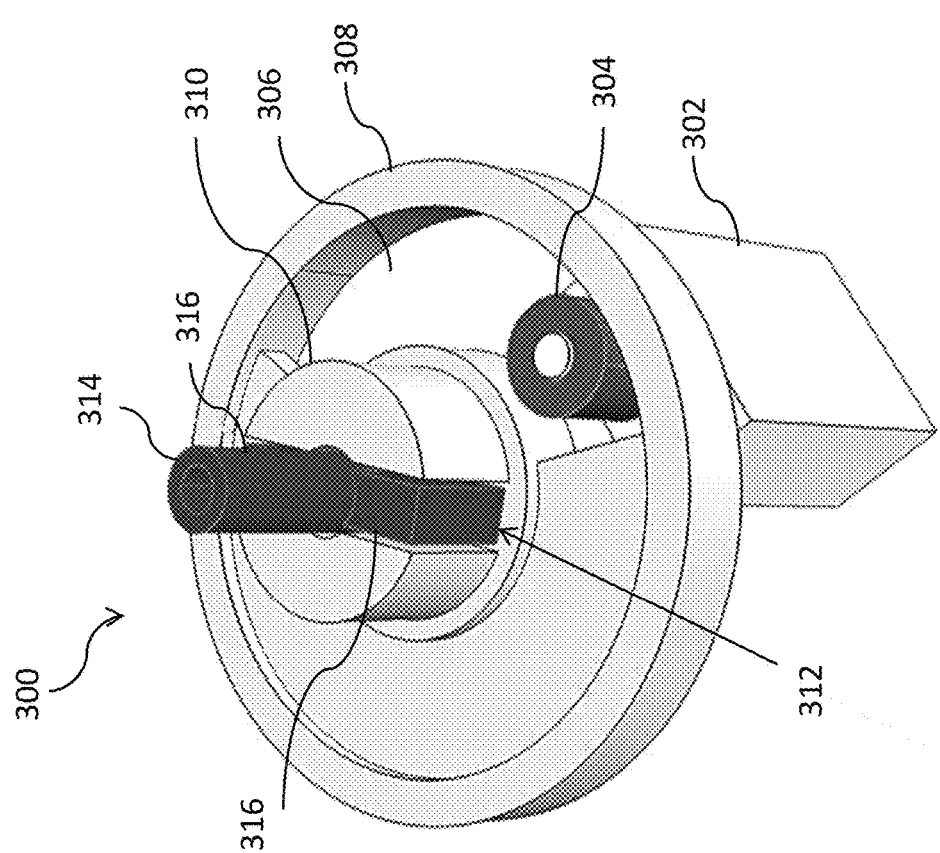
FIG. 7C is a top view of an embodiment of the motor assembly in the unlocked position.

Referring now to FIGS. 7B-7C, there is shown a side perspective view and a top view of the motor assembly 300 in the unlocked position. From the locked position, shown in FIG. 7B, the motor 302 is activated by an electrical signal from the printed circuit board 126, which rotates the gear 304 thereby rotating the internal gear wheel 308. The opening 306 in the internal gear wheel 308 limits rotation of the internal gear wheel 308 as it may only rotate in either direction until it catches on the gear 304. As the internal gear wheel 308 rotates, the lock 310 and keyway 312 rotate as well. The internal gear wheel 308 rotates until it is in the unlocked position, shown in FIG. 7B. In the unlocked position, the keys 316 of the shaft 314 of the pump assembly 120 are aligned with the keyway 312, which extends through the lock 310. Once the motor assembly 300 is in the unlocked position, the nozzle 108 can be compressed. Compression of the nozzle 108 causes the keys 316 on the shaft 314 of the pump assembly 120 to slide into the keyway 312 of the lock 310, as shown in FIG. 7C. When the nozzle 108 is released, the keys 316 on the shaft 314 slide out from the keyway 312 and the internal gear wheel 308 may be rotated back to the locked position shown in FIG. 7A.

Figure 8A:
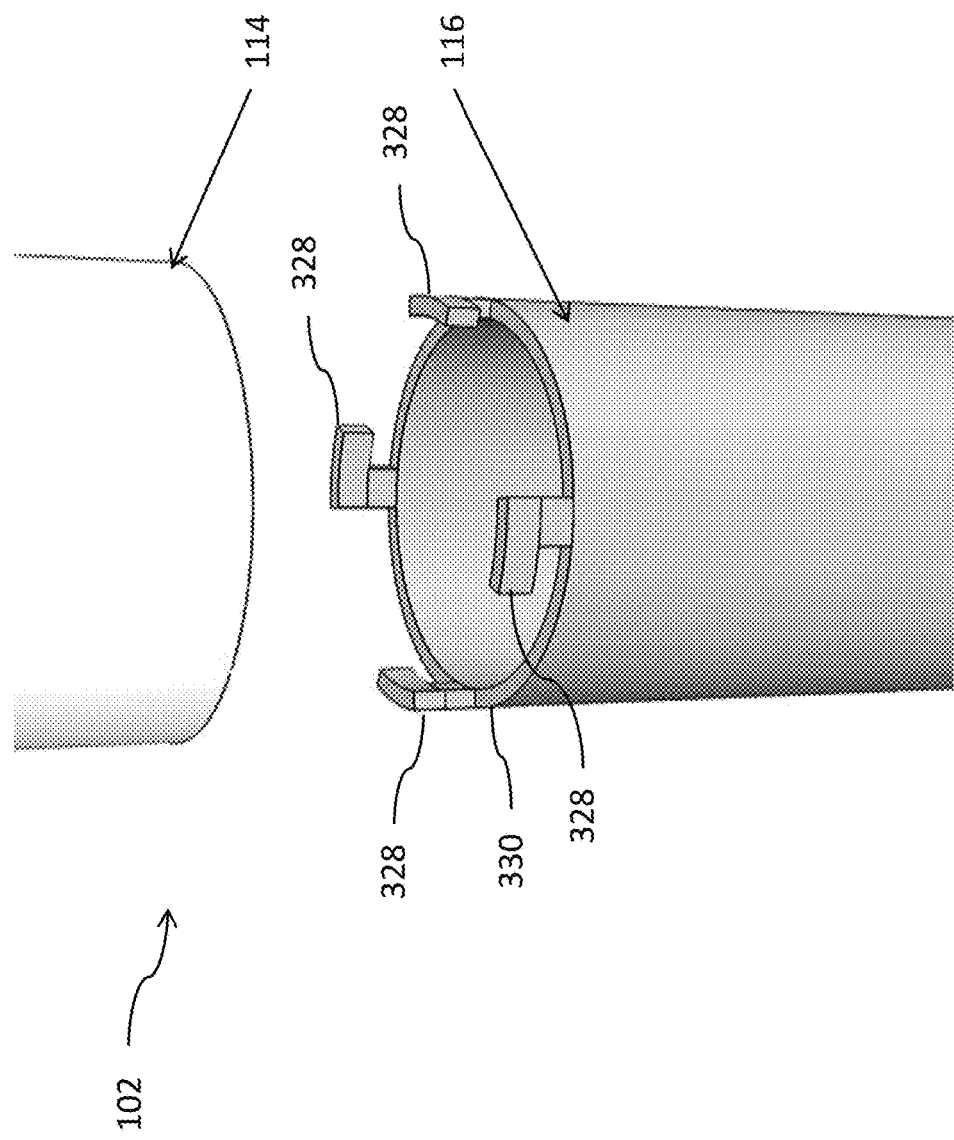
FIG. 8A is a side perspective view of an embodiment of the first and second portions of the housing having a motor assembly.
Figure 8B:
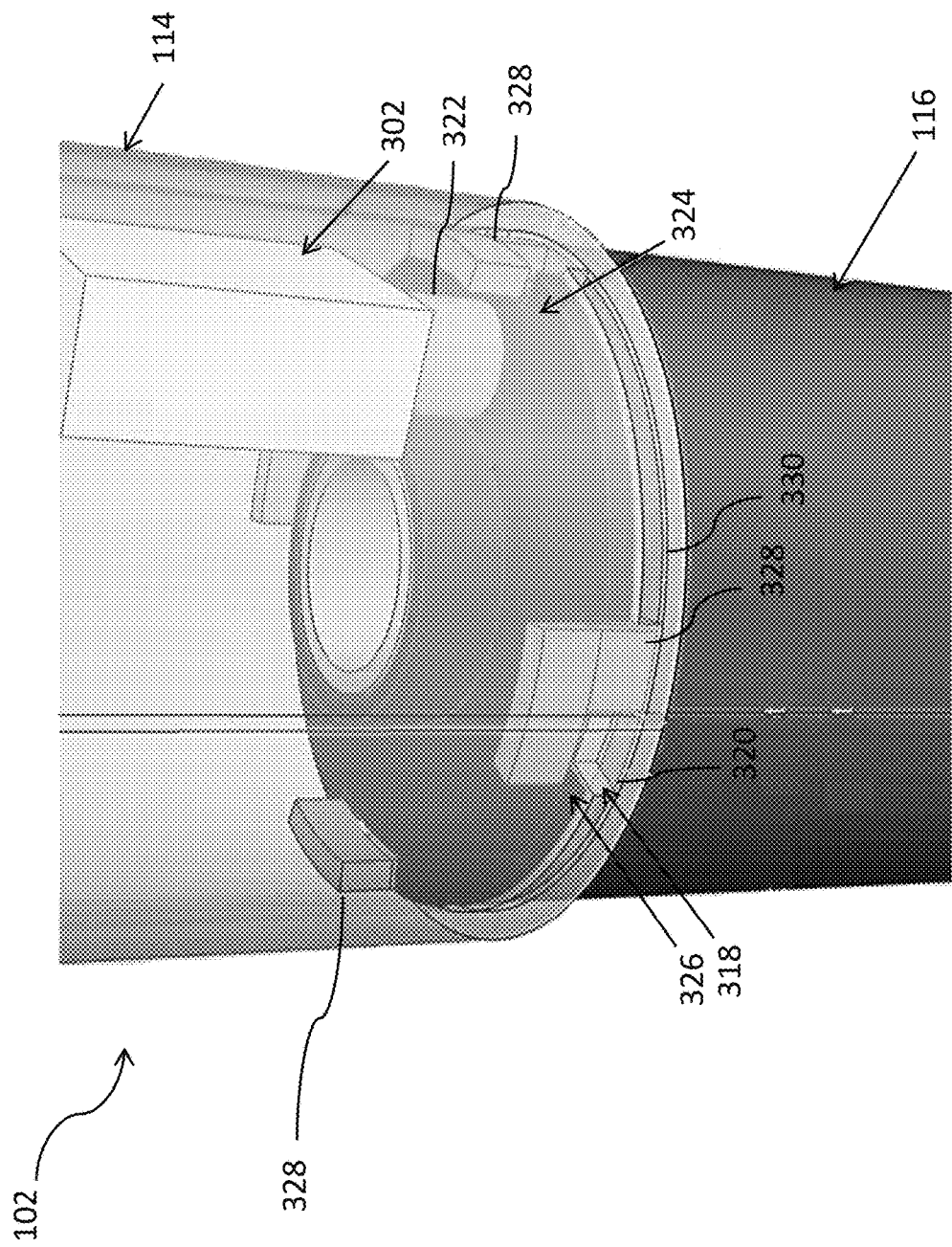
FIG. 8B is another side perspective view of an embodiment of the first and second portions of the housing in an unlocked position.
Figure 8C:
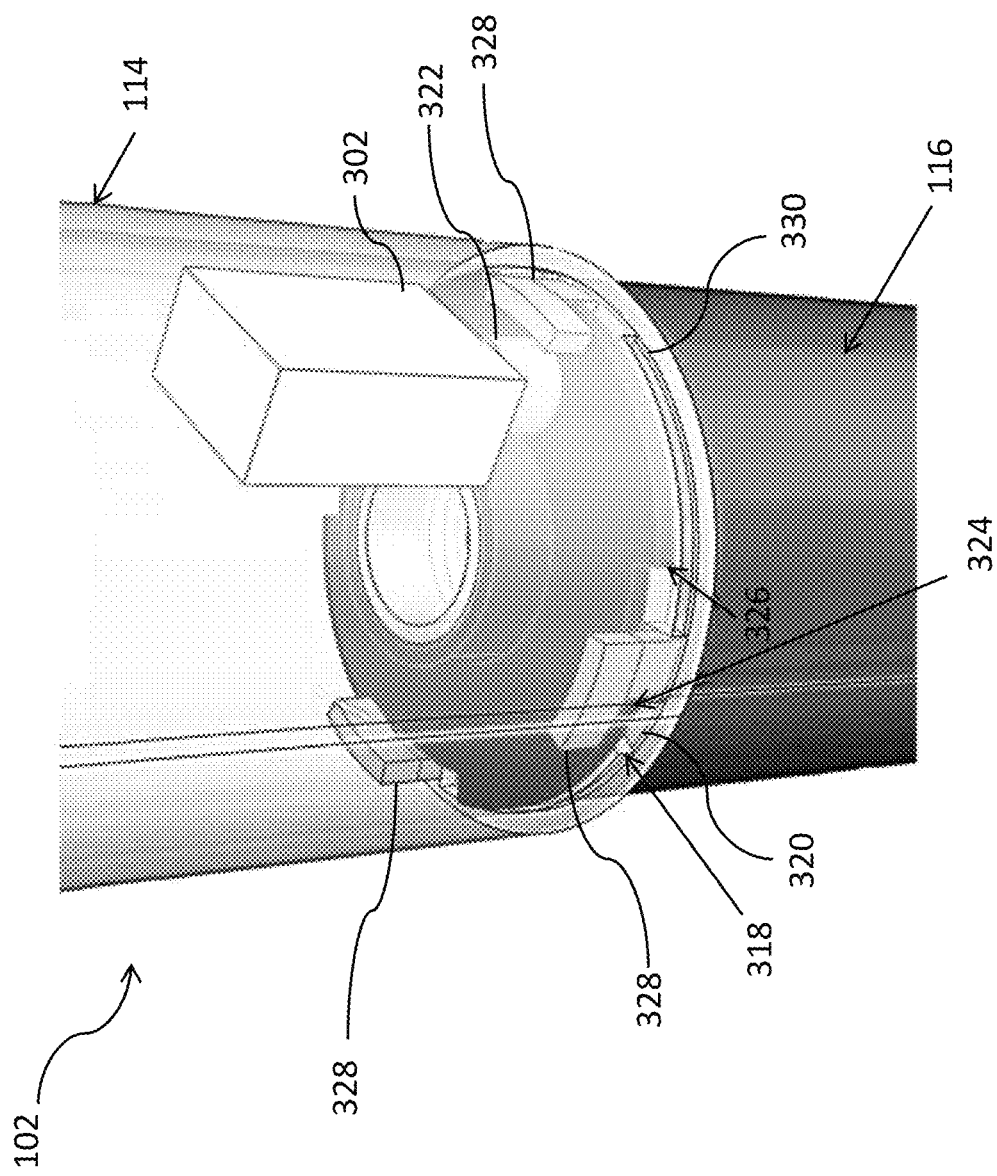
FIG. 8C is a top perspective view of an embodiment of the first and second portions of the housing in a locked position.

Turning now to FIGS. 8A-8C, there are shown various perspective views of the first portion 114 and second portion 116 of an embodiment of the housing 102 with a motor assembly 300. In the depicted embodiment, the first portion 114 of the housing 102 contains the pump assembly 102, the printed circuit board 126, and the battery 128 (not shown), and the second portion 116 of the housing 102 contains the liquid container 118 (not shown). Referring first to FIG. 8B, there is a side view of the first portion 114 of the housing 102 and the second portion 116 of the housing 102 in an unlocked position. The first portion 114 of the housing 102 has apertures 318 along the outer circumference of its bottom surface 320. A disc 324 stacked on top of the bottom surface 320 of the first portion 114 of the housing 102 has cutouts 326 along the outer circumference of the disc 324. The cutouts 326 which are configured to align with the apertures 318 in the bottom surface 320 of the first portion 114. Still referring to FIG. 8B, the motor 302 of the motor assembly 300 comprises a second gear 322 on a side of the motor 302 opposite the first gear 304. The second gear 322 is used to rotate the disc 324 on the bottom surface 320 of the first portion 114.

Referring now to FIG. 8A, the second portion 116 of the housing 102 comprises a plurality of L-shaped flanges 328 extending from the top surface 330 of the second portion 116. The L-shaped flanges 328 are configured to fit through the apertures 318 in the bottom surface 320 of the first portion 114 and the cutouts 326 in the disc 324. In the unlocked position, shown in FIG. 8B, the L-shaped flanges 328 are aligned with the apertures 318 in the bottom surface 320 of the first portion 114 and the cutouts 326 in the disc 324. Therefore, the second portion 116 can be pulled and removed from the first portion 114 of the housing 102.

To reach the locked position shown in FIG. 8C, the motor 302, upon receiving an electrical signal from the printed circuit board 126, rotates the second gear 422, which rotates the disc 324. The disc 324 rotates such that the cutouts 326 are no longer aligned with the L-shaped flanges 328. Therefore, the L-shaped flanges 328 and consequently, the second portion 116 of the housing 102, cannot be removed from the first portion 114. In some embodiments, the disc 324 is spring loaded such that the locked position is the default position of the disc 324.

The circuitry described to activate the locking mechanism may also be connected to one or more signal LEDs 130 on the housing 102, as shown in FIG. 1. In one embodiment, the signal LEDs 130 illuminate when the solenoid 124 is activated and the dispensing device 100 is in the locked position. In an alternative embodiment, the signal LEDs 130 may illuminate with color, such as red, when the solenoid 124 is activated and the dispensing device 100 is in the locked position, and green when the solenoid 124 is deactivated or otherwise inactive and the dispensing device 100 is in the unlocked position.

The circuitry also connects to and powers the screen 112 within the recess 110 on the housing 102. In the embodiments shown in FIGS. 2 and 3A, the recess 110 is enclosed by a lens 132. The lens 132 protects the screen 112 from liquid, debris, and other contaminants while still allowing a user to view the screen 112 clearly. In the depicted embodiment, the lens 132 is flush with the housing 102 to allow the user to easily manipulate the dispensing device 100. In one embodiment, the lens 132 may comprise a biometric sensor therein. In alternative embodiments, such as that shown in FIG. 1, the biometric sensor 134 is at a separate location along the housing 102. The biometric sensor 134 may include a fingerprint scanner, an iris scanner, a heart rate detector, and the like. The lens 132 may also comprise touchscreen capabilities such that the user may enter a passcode on a keypad displayed on the screen 112. The biometric sensor 134 and passcode elements provide an additional layer of security for access to the medication verifying the individual using the device and sending a signal to the printed circuit board 126 to move the solenoid 124 into the unlocked position.

In some embodiments, the dispensing device 100 may further comprise a photocell 136 located within the housing and connected to the circuitry. The photocell 136 detects light conditions inside the device. Thus, the photocell 136 can detect when the dispensing device 100 is tampered with or broken into. In other embodiments, the dispensing device 100 may further comprise a medication sensor 138 connected to the circuitry that monitors the level of medication in the liquid container 118. Thus, the medication sensor 138 can send a signal to the printed circuit board 126 when the liquid container 118 is empty or has a low volume of medication remaining.

The pump assembly 120 may additionally comprise a tactile switch 140. The tactile switch 140 operates as a momentary switch that it is activated when the pump assembly 120 is fully actuated. The tactile switch 140 is operably connected to the printed circuit board 126 where full actuations of the pump assembly 120 are recorded. Circuitry from the printed circuit board 126 additionally extends to a real-time clock chip 142. The real-time clock chip 142 can be used to provide the date and time for display on the screen 112. As will be discussed later, the real-time clock chip 142 can also be used in conjunction with the solenoid 124 and tactile switch 140 to lock the dispensing device 100.

Figure 4:
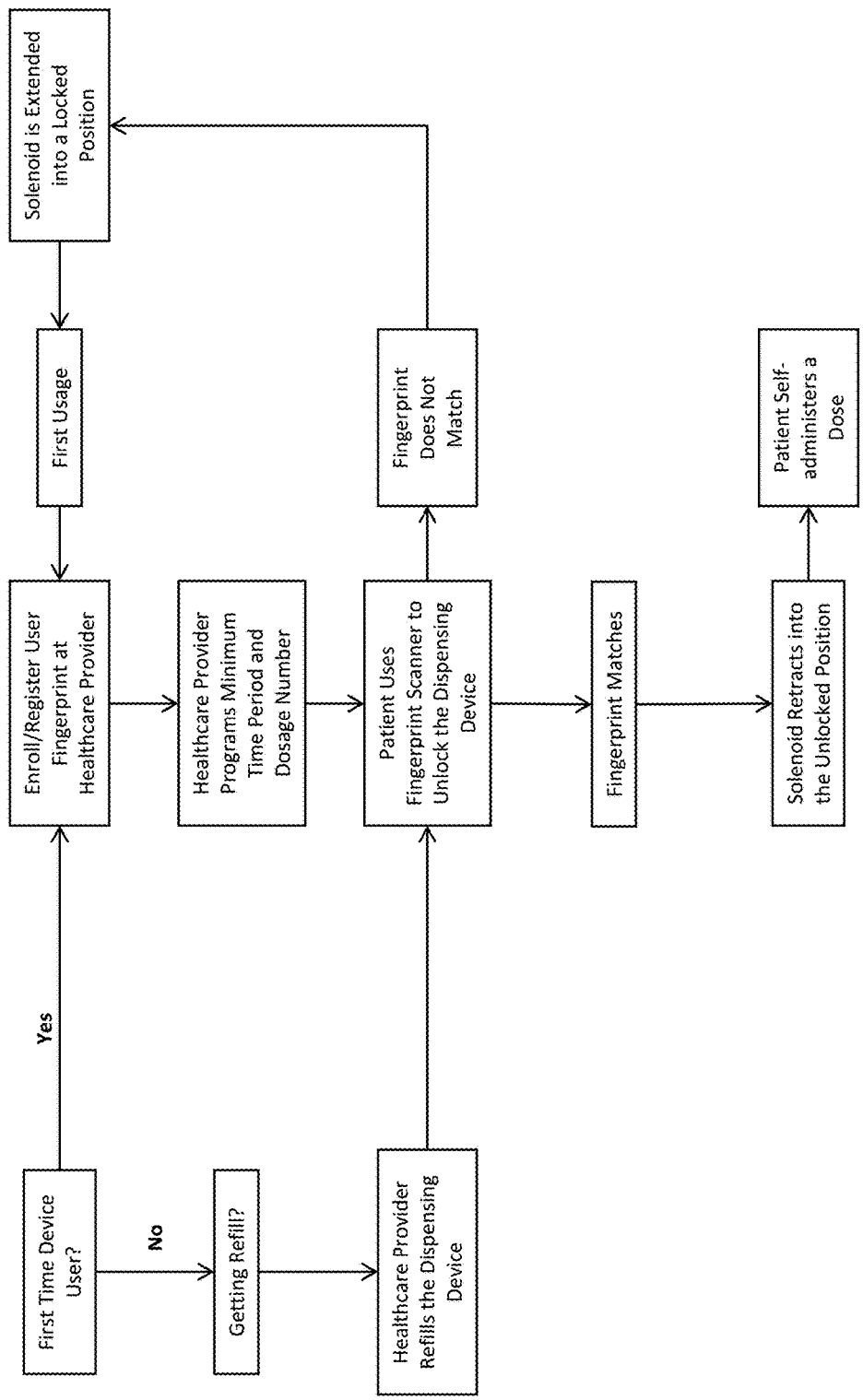
FIG. 4 is a diagram representation of an embodiment of the method according to the present invention.
Figure 5:
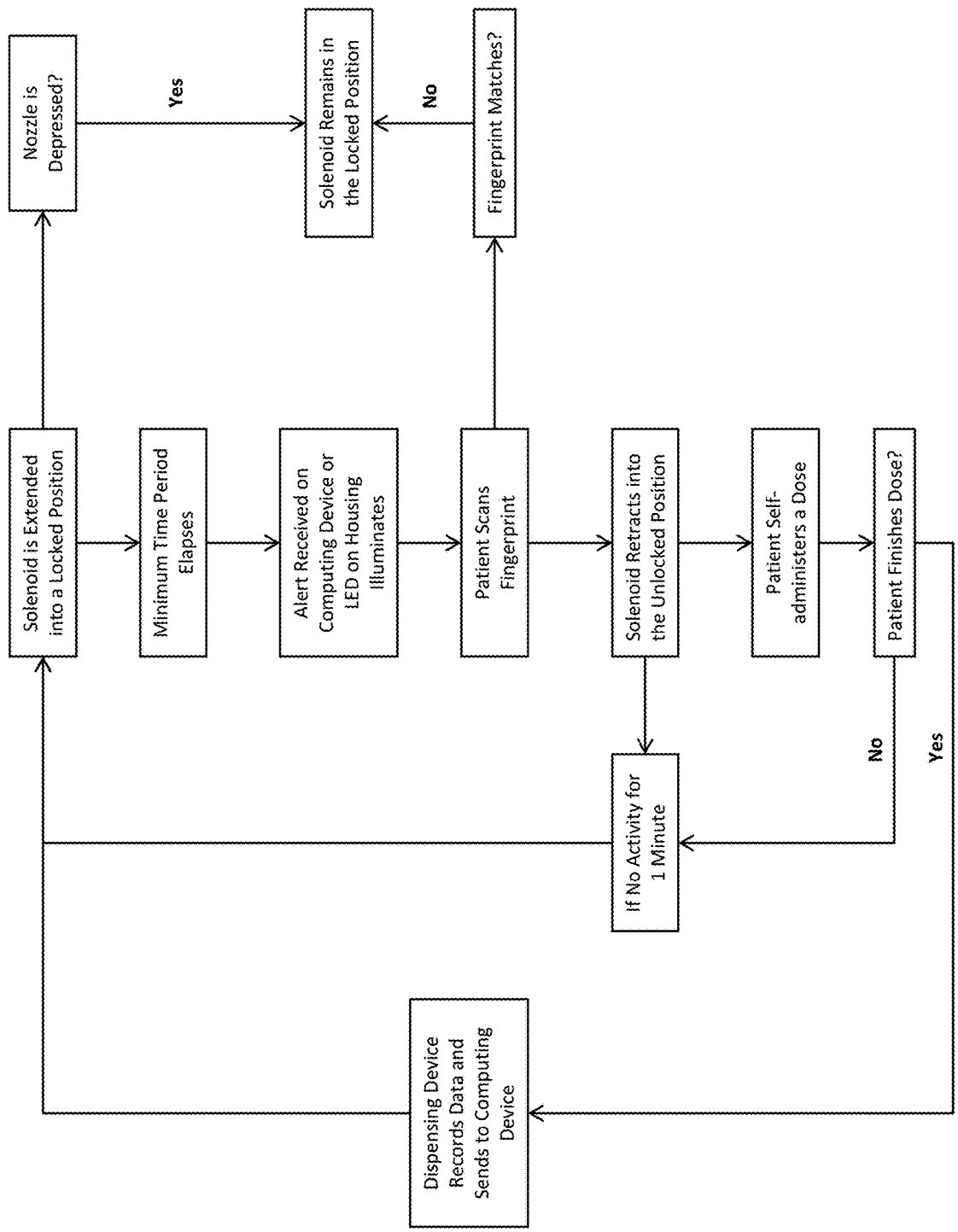
FIG. 5 is a diagram representation of an embodiment of the method according to the present invention.
Figure 6:
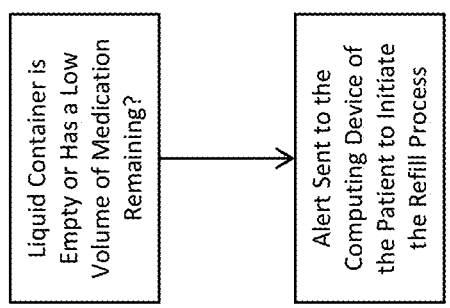
FIG. 6 is a diagram representation of an embodiment of the method according to the present invention.

Referring now to FIGS. 4-6, there are shown diagram representations of an embodiment of the method according to the present invention. In use, the components in the dispensing device 100 can communicate with a web platform accessible on the computing device 200 to control the dispensing of medication. The printed circuit board 126 may utilize Bluetooth low energy (BLE) as a wireless protocol to communicate with the computing device 200. Thus, the printed circuit board 126 can be programmed from the computing device 200. For example, a healthcare provider may adjust setting on the web platform via a terminal on a computing device 200. The healthcare provider may indicate a dosage number for the medication stored in the liquid container 118 and a minimum time period between dosages. This information is then transmitted to the printed circuit board 126. The printed circuit board 126 calculates the dosage number based on feedback from the tactile switch 140 and determines the time period between dosages based on data from the real-time clock chip 142.

In addition to programming the dispensing device 100, the web platform may be utilized by the healthcare provider to view status information from the dispensing device 100. For example, the dosage time, lock status, tamper alerts, and dosages remaining are information that may be pushed via a wireless network and/or cellular data from the dispensing device 100 to the web platform, which is ultimately accessible by the healthcare provider at a terminal on the computing device 200. In addition, the web platform may also include a calendar interface, or other scheduling format, for tracking patient dosages and prescription regimens. Thus, the dispensing device 100, the healthcare provider's computing device 200, and a patient's smartphone (as explained below) may exchange status information via GSM or some other similar digital cellular network.

The biometric sensor 134 may be programmed by the patient in the presence of the healthcare provider. For example, the healthcare provider can adjust settings on the web platform to allow for programming of the biometric sensor 134. The biometric sensor 134 can then scan the fingerprint of the patient, for example, to assign the patient identity to the particular dispensing device 100. Once programmed, the biometric sensor 134 will require identity verification before the dispensing device 100 can be used.

Once the dispensing device 100 is programmed via the web platform on the healthcare provider's computing device 200, the patient may use the dispensing device 100. To access the medication, the patient will first prove his or her identity by actuating the biometric sensor 134, such as placing a finger on the biometric sensor 134 for fingerprint scanning verification. Once the patient's identity is verified, the patient can self-administer the first dose of medication.

In an alternative embodiment, the patient's smartphone or other computing device may serve as a second layer of authentication to utilize the dispensing device 100. For example, the patient may have access to a patient interface of the web platform on his or her smartphone. At the dosing time, the patient may be required to authenticate himself or herself via the smartphone. For example, the patient may complete authentication by unlocking his or her phone via a passcode or fingerprint sensor. In another embodiment, the healthcare provider may send a temporary or one-use PIN code from the healthcare provider interface of the web platform to the patient interface of the web platform. Therefore, the patient can access the web platform on his or her smartphone, retrieve the PIN code, and enter the PIN code on the dispensing device 100 to unlock it.

To administer the first dose, the patient holds the dispensing device 100 such that the nozzle 108 is close to or partially within the nostril and applies pressure to the nozzle 108 towards the surface 104a of the first closed end 104. The pump assembly 120 expels medication from the nozzle 108 such that the patient may inhale the medication. When the pump assembly 120 is actuated, the tactile switch 140 is also triggered. The tactile switch 140 sends a signal to the printed circuit board 126 that the pump assembly 120 has been actuated, indicating that a dosage has been administered. Simultaneously, the printed circuit board 126 associates the signal from the tactile switch 140 with the time provided by the real-time clock chip 142.

If the healthcare provider has set a minimum time period between dosages, receipt of the signal from the tactile switch 140 will also cause the printed circuit board 126 to actuate the solenoid 124. The solenoid 124 will move into the path of the nozzle 108 thereby preventing the patient from administering a subsequent dose of medication. The dispensing device 100 will remain in the locked position with the solenoid 124 blocking the actuation of the nozzle 108 until the minimum time period has elapsed. The printed circuit board 126 can monitor the time using data received from the real-time clock chip 142. Once the minimum time period has elapsed after actuation of the tactile switch 140, the printed circuit board 126 will trigger the solenoid 124 to retract thereby allowing the patient to fully depress the nozzle 108 to administer a subsequent dosage. Thereafter, the locking process is repeated.

In embodiments wherein one or more signal LEDs 130 are located on the housing 102, the signal LEDs may illuminate a red color when the solenoid 130 is in the path of the nozzle 108, indicating that a dosage may not be administered, and a green color when the solenoid 124 is retracted, signaling to the patient that a subsequent dosage is available. As the printed circuit board 126 can wirelessly communicate with a computing device 200, a signal from the printed circuit board 126 can be transmitted to the computing device 200 alerting the patient that the next dosage is available. In an alternative embodiment, the medication sensor 138 may transmit a signal to the printed circuit board 126 and ultimately to the computing device 200 indicating that the liquid container 118 is empty or has a low volume of medication remaining. This alerts the patient to initiate the process of refilling the prescription.

In embodiments wherein the housing 102 comprises a photocell 136, the photocell 136 can be configured to send a signal to the printed circuit board 126 when the photocell 136 detects light above a programmed threshold. The printed circuit board 126 can be programmed to transmit a signal to a computing device 200 accessible by the healthcare provider. The signal can manifest as an alert on the web platform notifying the healthcare provider that the dispensing device 100 has been tampered with. In additional embodiments, the printed circuit board 126 may be programmed to send data from any component or combination of components of the dispensing device 100 to a computing device 200 operated by the healthcare provider and/or by the patient. The healthcare provider and the patient can then access this data to improve compliance with the treatment plan.

While embodiments of the present invention has been particularly shown and described with reference to certain exemplary embodiments, it will be understood by one skilled in the art that various changes in detail may be effected therein without departing from the spirit and scope of the invention as defined by claims that can be supported by the written description and drawings. Further, where exemplary embodiments are described with reference to a certain number of elements it will be understood that the exemplary embodiments can be practiced utilizing either less than or more than the certain number of elements.

What is claimed is:

1. A system for a time-controlled medication dispensing, comprising: a computing device;
    a dispensing device wirelessly connected to the computing device, the dispensing device comprising:
        a cylindrical housing with a first closed end and a second closed end;
        wherein the first closed end has a surface and a nozzle which moves perpendicular relative to the surface;
        a liquid container within the cylindrical housing having a pump assembly connected thereto, the pump assembly actuable through movement of the nozzle toward the surface;
        a processor located within the cylindrical housing and configured to actuate a locking mechanism within the cylindrical housing according to instructions transmitted from the computing device, wherein the locking mechanism comprises a motor assembly having a motor which rotates a gear within an internal gear wheel, and further comprising a lock on the internal gear wheel, the lock having a keyway and a shaft on the pump assembly having one or more keys configured to fit within the keyway; and
    wherein, in a locked position, the locking mechanism blocks the nozzle from depressing to the surface of the first closed end.

2. The system of claim 1, wherein, in an unlocked position, the locking mechanism does not block the nozzle from moving to the surface of the first closed end.

3. The system of claim 1, wherein, in the unlocked position, the keys are aligned with the keyway.

4. The system of claim 1, wherein, in the locked position, the keys are not in alignment with the keyway.

5. The system of claim 4, wherein the instructions are a dosage schedule.

6. A system for a time-controlled medication dispensing, comprising:
   a computing device;
   a dispensing device wirelessly connected to the computing device, the dispensing device comprising:
      a nozzle, which moves perpendicular to a surface of a cylindrical housing with a first portion and a second portion, the first portion having a pump assembly connected to the nozzle and the second portion having a liquid container therein connected to the pump assembly;
      a processor located within the first portion of the housing, operably connected to a power source and configured to actuate a locking mechanism within the cylindrical housing according to instructions transmitted from the computing device, wherein the locking mechanism is a motor assembly and the motor assembly comprises a motor connected to a first gear, which is rotatable by the motor within an internal gear wheel, a lock on the internal gear wheel, the lock having a keyway, and a shaft on the pump assembly having one or more keys configured to fit within the keyway;
      wherein, the locking mechanism moves from a locked position to an unlocked position when actuated by the processor.

7. The system of claim 6, wherein, in the locked position, the locking mechanism blocks the nozzle from moving to the surface of the cylindrical housing.

8. The system of claim 6, further comprising:
   a second gear connected to both the motor and a disc on a bottom surface of the first portion.

9. The system of claim 8, further comprising:
   one or more cutouts along an outer circumference of the disc;
   apertures in the bottom surface of the first portion; and
   one or more flanges along a top surface of the second portion;
   wherein the flanges are configured to slide through the apertures in the bottom surface of the first portion and the cutouts in the disc when the apertures and the cutouts are aligned.

10. The system of claim 9, wherein rotation of the second gear by the motor, rotates the disc and the cutouts out of alignment with the apertures, locking the flanges in the first portion of the cylindrical housing.

11. A method for controlled medical therapy, comprising the steps of:
   providing a system comprising a computing device and a dispensing device wirelessly connected to the computing device, the dispensing device comprising a cylindrical housing with a first closed end and a second closed end, wherein the first closed end has a surface and a nozzle which moves perpendicular relative to the surface, a liquid container within the cylindrical housing having a pump assembly connected thereto, the pump assembly actuable by movement of the nozzle toward the surface, and a processor located within the cylindrical housing and configured to actuate a locking mechanism comprising a motor assembly, wherein the motor assembly comprises a motor connected to a first gear, which is rotatable by the motor within an internal gear wheel, a lock on the internal gear wheel, the lock having a keyway, and a shaft on the pump assembly having one or more keys configured to fit within the keyway;
   transmitting an authentication key from the computing device to the processor of the dispensing device;
   transmitting instructions from the computing device to the processor of dispensing device;
   verifying an identity via the authentication key;
      moving the locking mechanism, by the processor, to an unlocked position according to the instructions from the computing device;
   depressing the nozzle toward the surface of the first closed end of the cylindrical housing;
   expelling a substance from the liquid container through the nozzle via the pump assembly.

12. The method of claim 11, wherein the step of depressing the nozzle toward the surface of the first closed end of the cylindrical housing includes activating a tactile switch, which sends a signal to the processor of the dispensing device.

13. The method of claim 12, further comprising a step of transmitting a signal from the processor to the locking mechanism causing the locking mechanism to move to a locked position.

14. The method of claim 12, further comprising a step of maintaining, by the processor, the locking mechanism in a locked position according to the instructions from the computing device.

\* \* \* \* \*